(12) United States Patent
Jansen et al.

(10) Patent No.: US 7,104,979 B2
(45) Date of Patent: *Sep. 12, 2006

(54) CATHETER WITH COMPOSITE STIFFENER

(75) Inventors: Lex P. Jansen, Pleasanton, CA (US); Thomas Yung-Hui Chien, San Jose, CA (US); Perry Alvin Fukui, Fremont, CA (US); Jeffrey A. Sarge, Fremont, CA (US); Lawrence Charles Alpert, Fremont, CA (US)

(73) Assignee: Target Therapeutics, Inc., Fremont, CA (US)

( * ) Notice: Subject to any disclaimer, the term of this patent is extended or adjusted under 35 U.S.C. 154(b) by 604 days.

This patent is subject to a terminal disclaimer.

(21) Appl. No.: 10/079,103

(22) Filed: Feb. 19, 2002

(65) Prior Publication Data

US 2002/0123738 A1   Sep. 5, 2002

Related U.S. Application Data

(63) Continuation of application No. 09/096,267, filed on Jun. 11, 1998, now Pat. No. 6,368,316.

(51) Int. Cl.
*A61M 25/00* (2006.01)

(52) U.S. Cl. .................... 604/525; 604/526; 604/527

(58) Field of Classification Search ........ 604/523–528, 604/264; 138/118, 123, 124, 129, 140–141, 138/143, 144, 172–173
See application file for complete search history.

(56) References Cited

U.S. PATENT DOCUMENTS

| | | | |
|---|---|---|---|
| 2,407,929 A | 9/1946 | Jeckel |
| 2,437,542 A | 3/1948 | Krippendorf |
| 2,458,305 A | 1/1949 | Sanders |
| 3,174,851 A | 3/1965 | Buehler et al. |
| 3,351,463 A | 11/1967 | Rozner et al. |
| 3,416,531 A | 12/1968 | Edwards |
| 3,753,700 A | 8/1973 | Harrison et al. |
| 4,484,586 A | 11/1984 | McMickle et al. |
| 4,516,972 A | 5/1985 | Samson |
| 4,739,768 A | 4/1988 | Engelson |
| 5,019,057 A | 5/1991 | Truckai |
| 5,057,092 A | 10/1991 | Webster, Jr. |
| 5,069,674 A | 12/1991 | Fearnot et al. |
| 5,078,700 A | 1/1992 | Lambert et al. |
| 5,176,660 A | 1/1993 | Truckai |
| 5,248,305 A | 9/1993 | Zdrahala |
| 5,254,107 A | 10/1993 | Soltesz |

(Continued)

FOREIGN PATENT DOCUMENTS

EP     0715868 A     6/1996

(Continued)

*Primary Examiner*—LoAn H. Thanh
(74) *Attorney, Agent, or Firm*—Crompton, Seager & Tufte, LLC

(57) ABSTRACT

A catheter comprising an elongate tubular member having a proximal end, a distal end, and a passageway defining a lumen extending between the proximal and distal ends. The elongate tubular member comprises a relatively stiff proximal section and a relatively flexible distal section. The proximal section includes an inner tubular liner, a first stiffener comprising a metal alloy, and a second stiffener comprising a non-metal alloy. The first and second stiffeners are coaxially wound exterior to the proximal inner liner. The distal section includes a distal inner tubular liner and the second stiffener coaxially wound exterior to the distal inner liner. The first stiffener terminates before reaching the distal section.

41 Claims, 6 Drawing Sheets

U.S. PATENT DOCUMENTS

| | | |
|---|---|---|
| 5,308,342 A | 5/1994 | Sepetka et al. |
| 5,312,356 A | 5/1994 | Engelson et al. |
| 5,454,795 A * | 10/1995 | Samson ................... 604/526 |
| 5,462,523 A | 10/1995 | Samson et al. |
| 5,526,849 A * | 6/1996 | Gray ........................ 138/133 |
| 5,538,513 A | 7/1996 | Okajima |
| 5,558,737 A | 9/1996 | Brown et al. |
| 5,695,483 A | 12/1997 | Samson |
| 5,702,373 A | 12/1997 | Samson |
| 5,704,926 A | 1/1998 | Sutton |
| 5,711,909 A | 1/1998 | Gore et al. |
| 5,733,400 A | 3/1998 | Gore et al. |
| 5,951,539 A | 9/1999 | Nit et al. |
| 6,143,013 A * | 11/2000 | Samson et al. ............. 606/192 |

FOREIGN PATENT DOCUMENTS

| | | |
|---|---|---|
| EP | 0815894 | 1/1998 |
| WO | WO 9638194 A | 12/1996 |

* cited by examiner

CATHETER WITH COMPOSITE STIFFENER

FIELD OF THE INVENTION

This invention relates generally to catheters, and more particularly, to a catheter with a composite stiffener.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PTA). Such a procedure uses catheters having balloons on their distal tips. It is similarly common that those catheters are used to deliver a radiopaque agent to the site in question prior to the PTA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the vascular system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter.

This invention is an adaptable one and may be used in a variety of catheter formats. The construction technique has the benefit of producing catheter sections having small overall diameters but with exceptional strength, resistance to kinking, and recovery from kinking (even in vivo) should such kinking occur. The catheter may be used in conjunction with a guidewire, but the catheter may also be used as a flow-directed catheter with the attachment of a balloon or in combination with a specifically flexible tip.

The use of a braid or coil in a catheter body is not a novel concept. Typical background patents are discussed below. However, none of these documents have used the concept of this invention to produce a catheter having the structure and physical capabilities of the catheter of this invention.

U.S. Pat. No. 5,454,795 discloses a kink-free spiral wound catheter. The catheter includes a stiffener ribbon, typically metallic, spirally wound within the catheter body to create a catheter having controllable stiffness. The stiffener is included in a distal section of the catheter U.S. Pat. No. 5,702,373 shows a catheter having a reinforced braid typically of superelastic alloy ribbon located in a distal section of the catheter. The superelastic alloy ribbon provides high resistance to kinking.

SUMMARY OF THE INVENTION

This invention is a catheter having a) a more proximal section preferably made up of an inner tubular liner, a first stiffener comprising a metal alloy, and a second stiffener comprising a non-metal alloy, the first and second stiffeners being coaxially wound exterior to the proximal inner liner; and b) a more distal section comprising a distal inner tubular liner, and the second stiffener coaxially wound exterior to the distal inner liner. The first stiffener desirably terminates before reaching the distal section to provide a more flexible distal section. Other sections of these or other designs may be placed variously between the noted sections or distal of the distal section described above.

The stiffeners may be wound in a number of different ways. For example, the stiffener may comprise a single strand of ribbon wound in a single direction or multiple strands interwoven in a braid. The first and second stiffeners may be independently wound as a coil or braid or may be interwoven to form a single braid. The first stiffener may include ribbons formed of a superelastic alloy such as nitinol, for example. The metal stiffener provides kink resistance to the proximal section of the catheter. The second stiffener may include a polymer such as liquid crystal polymer, polyurethane, polyimide, polyethylene, polyethylene terephthalate, or Nylon, for example. The second stiffener is desirably made from a material which is capable of being permanently deformed when exposed to steam so that the catheter may be shaped to have various bends for a specific surgical procedure.

The catheter may also have an outer cover exterior to the stiffener. The inner tubular liner and outer cover may be of a polymeric composition. A lubricious coating may be applied to the outer surface of the outer cover or the inner surface of the inner liner.

The catheter assembly may also have such ancillary components as a luer-lock and some manner of providing radiopacity.

The above is a brief description of some deficiencies in the prior art and advantages of the present invention. Other features, advantages, and embodiments of the invention will be apparent to those skilled in the art from the following description, drawings and claims.

BRIEF DESCRIPTION OF THE DRAWINGS

Corresponding reference characters indicate corresponding parts throughout the several views of the drawings.

DESCRIPTION OF THE INVENTION

This invention is a catheter assembly having a more distal section preferably made up of an inner liner, an outer cover, and a stiffener comprising a non-metal alloy, and a more proximal section comprising an inner liner, an outer cover, and a stiffener comprising a metal alloy and a non-metal alloy. The stiffeners are interposed between the inner liner and outer cover. Other sections of these or other designs may be placed variously between the noted sections or distal of the distal section noted above.

Figure 1:
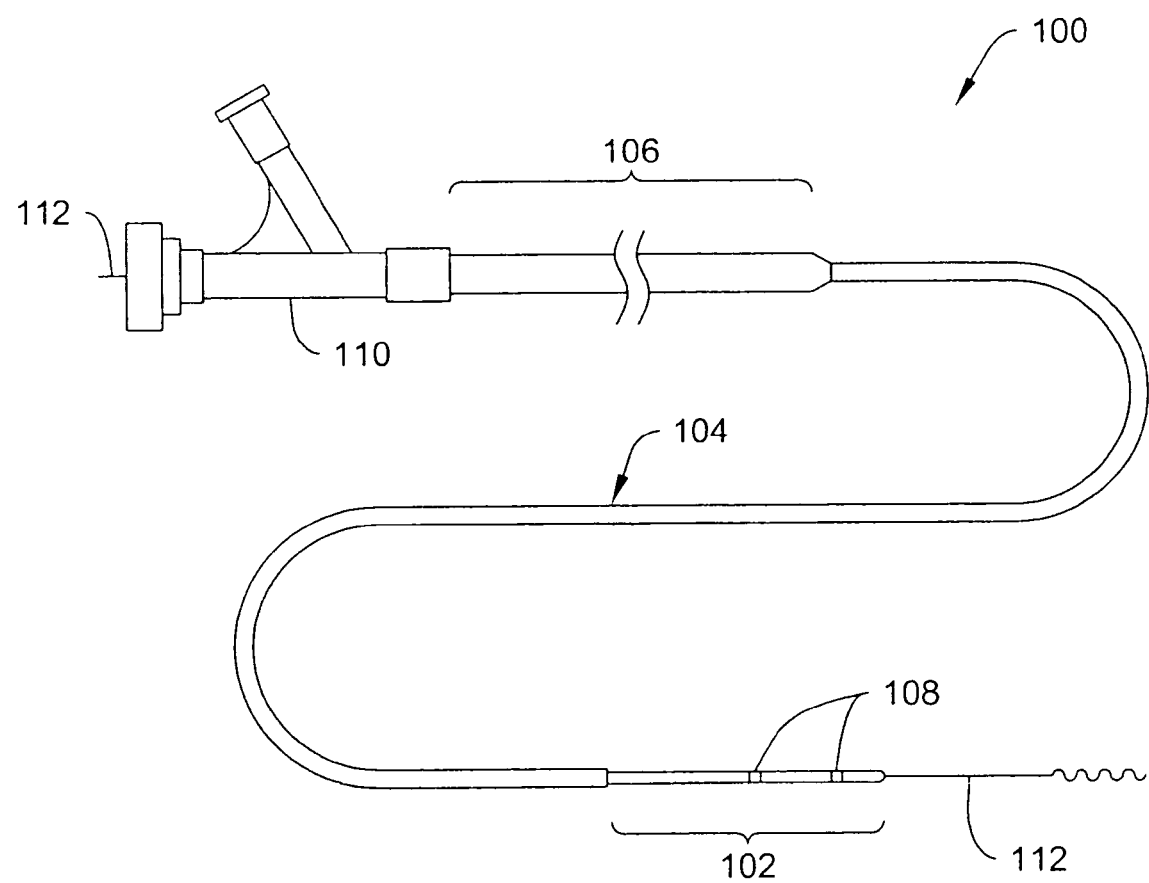
FIG. 1 is a side view of a typical three section catheter made using the concepts of this invention.

A typical multi-section catheter 100 which may incorporate the concepts of this invention is shown in FIG. 1. Such a catheter is described in more detail in U.S. Pat. No. 4,739,768, to Engelson, the entirety of which is incorporated by reference and is particularly suitable for neurological and peripheral vascular applications. It is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever smaller vascular areas. This smaller diameter requires a concomitant thinning of the wall section. The thinner section walls may kink or ripple when actively pushed along the guidewire or when vaso-occlusive devices are pushed through the catheter's lumen. The typical configuration shown in FIG. 1 has a distal section 102 having significant flexibility, an intermediate section 104 which is typically less flexible, and a long proximal section 106 which in turn is least flexible. The distal section 102 is flexible and soft to allow deep penetration of the extraordinary convolutions of the neurological vasculature without trauma. Various known and often necessary accessories to the catheter assembly, e.g., one or more radiopaque bands 108 at the distal region to allow viewing of the position of the distal region under fluoroscopy and a luer assembly 110 for guidewire 112 and fluids access, are also shown in FIG. 1. The typical dimensions of this catheter are:

| | |
|---|---|
| Overall length: | 60–200 cm |
| Proximal Section (106): | 30–150 cm |
| Intermediate Section (104): | 20–50 cm |
| Distal Section (102): | 2.5–30 cm |

Obviously, these dimensions are not particularly critical to this invention and are selected as a function of the malady treated and its site within the body. Typical of the catheters made using this invention are those in the 2 French to 5 French range (1 French=0.013 inch). The inner diameter of such catheters is then 10 mils. to 42 mils. (1 mil=0.001 inch).

Furthermore, a catheter made using this inventive concept need not be of three sections with increasing stiffness as is shown in FIG. 1. The catheter may be of two discrete sections or may be of four or more discrete sections of differing flexibility. Through judicious choice of physical parameters for the catheter sections, the components may also have varying physical parameters (e.g., lubricity, flexibility, wall thickness, inner or outer layer member composition, etc.) within the sections. Typically, although not necessarily, when a three section catheter is desired, the most proximal section 106 is the "more proximal" or "stiff" section described herein. Again, although not necessarily, when a three section catheter is desired, the most distal section 102 is the "more distal" or "flexible" section. The distal section 102 may be the distal end of the catheter.

Figure 2:
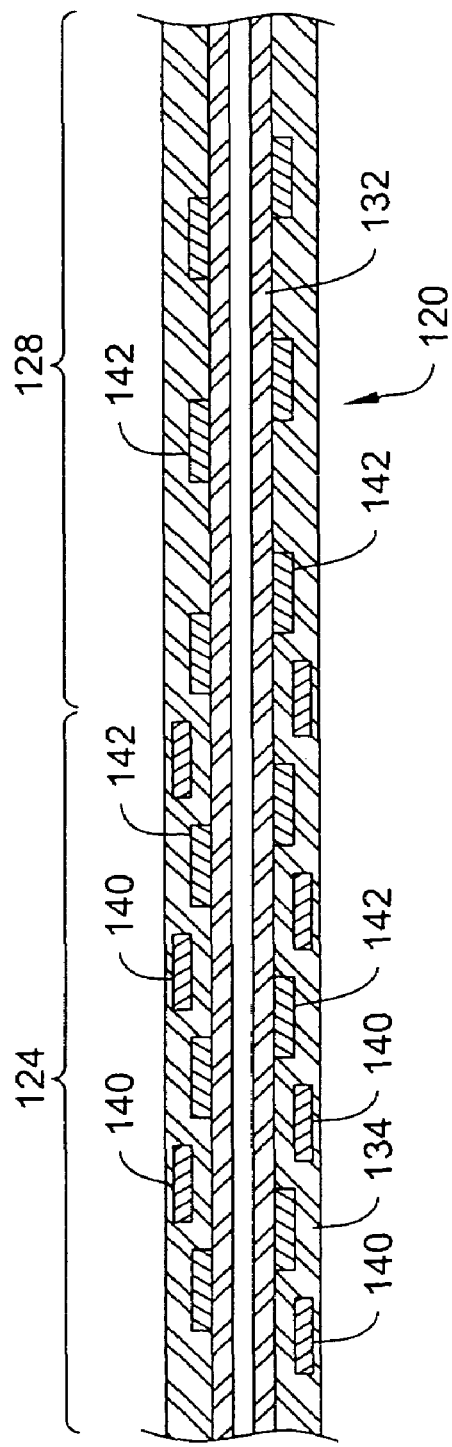
FIG. 2 is a schematic cross-sectional view of proximal and distal sections of a catheter.
Figure 3:
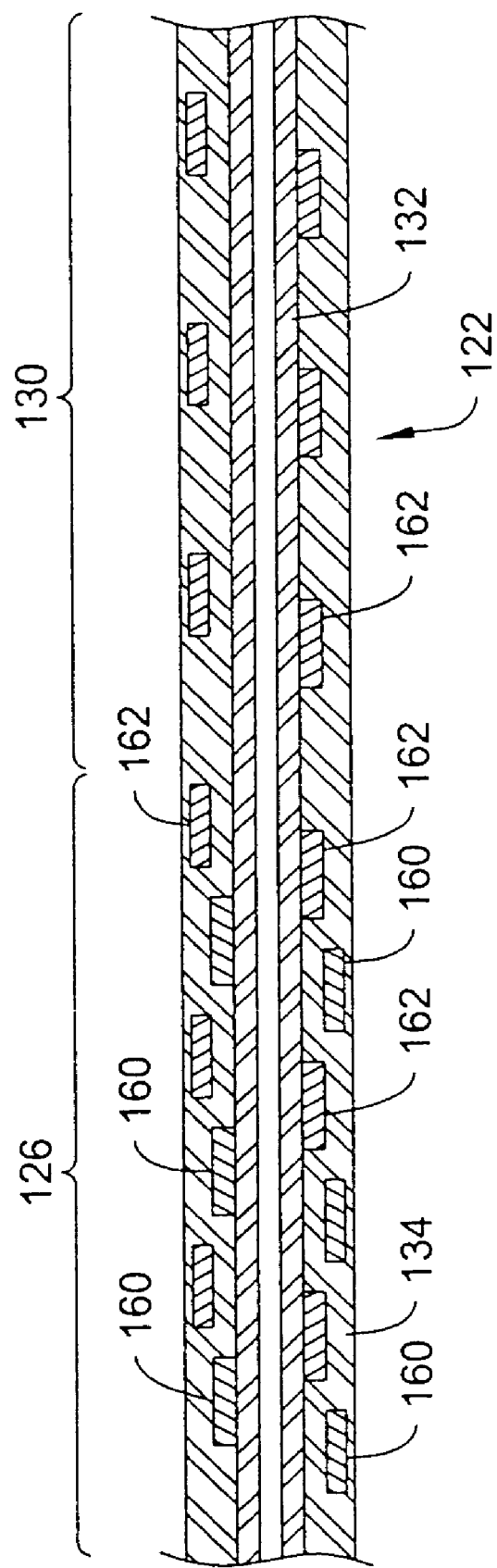
FIG. 3 is a schematic cross-sectional view of alternate proximal and distal sections of a catheter.

FIGS. 2 and 3 illustrate two catheter portions, generally indicated at 120 and 122, and having a proximal section 124, 126 and a distal section 128, 130, respectively. The distal section 128, 130 may be at the distal end of the catheter, or there may be another section located distally of the distal section. The catheter portions are elongate tubular members having a proximal end, a distal end, and a passageway defining a lumen extending between the proximal and distal ends. Referring to FIG. 2, the catheter portion 120 preferably includes an inner tubular liner 132, an outer cover 134, and a stiffener coaxially wound and interposed between the inner liner and the outer cover. The stiffener is formed from a first stiffener 140 comprising a metal alloy and a second stiffener 142 comprising a non-metal alloy. The metal stiffener 140 terminates before reaching the distal section 128 so that only the non-metal stiffener 142 is located within the distal section. This allows the distal section 128 to be heated by, for example, exposure to steam, and permanently deformed so that the distal section can be bent into a specific configuration corresponding to vasculature through which the catheter is to be inserted. For example, the distal section 128 of the catheter may be exposed to steam (212° F.) and formed around a mandrel. This allows the shaping of the distal section 128 to be accomplished at the time of surgery while the vasculature is being viewed. The metal stiffeners which are typically present in conventional catheters prevent the reshaping of the distal section of the catheter since the metal itself can not be reshaped by steam heating.

The stiffener may be formed with one or more coils or braids. For example, a metal strand may be helically wound onto the inner liner 132, and a non-metal strand may be helically wound on top of the metal strand. Alternatively, the stiffener may be formed from a metal strand interwoven with a non-metal strand to form a braid. The first and second stiffeners may also be individually formed as a separate braid from two or more strands. It is to be understood that the shape of the strands, number of strands, and arrangement of the strands may be different than shown in FIGS. 2 and 3 or described herein without departing from the scope of the invention. For example, the strand may be a wire having a circular or oval cross-sectional shape. Typical coil and braid stiffeners which may be used in the proximal or distal sections are shown in FIGS. 4–6.

Figure 4:
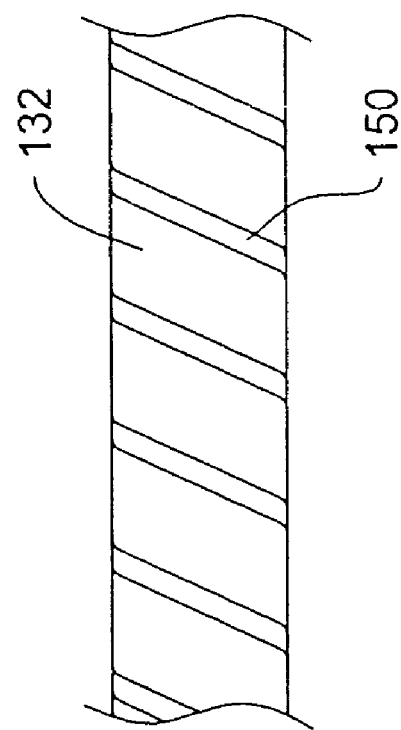
FIG. 4 is an enlarged side view of a section of a catheter having a ribbon helically wound on an inner tubular liner.

FIG. 4 shows a magnified section of a catheter body which may be used as a distal section of a catheter. The catheter section includes the inner tubular liner 132 and a stiffener which comprises a helically wound ribbon 150. The ribbon 150 may be simply wound onto the inner liner 132 or the ribbon may be applied with an adhesive. The number of turns or pitch of the ribbon 150 may vary along the length of the section or catheter to control the overall stiffness of the section or catheter.

Figure 5:
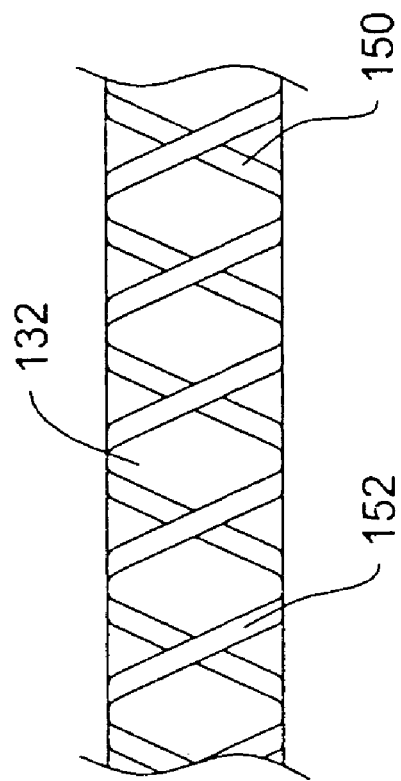
FIG. 5 is an enlarged side view of the section of FIG. 4 with a second ribbon helically wound over the first ribbon.

FIG. 5 shows the catheter section of FIG. 4 with the helically wound stiffener ribbon 150 wound in a first direction or "handedness" and a second stiffener ribbon 152 wound in a second direction or "handedness" around both the first stiffener ribbon and the inner tubular liner 132.

Figure 6:
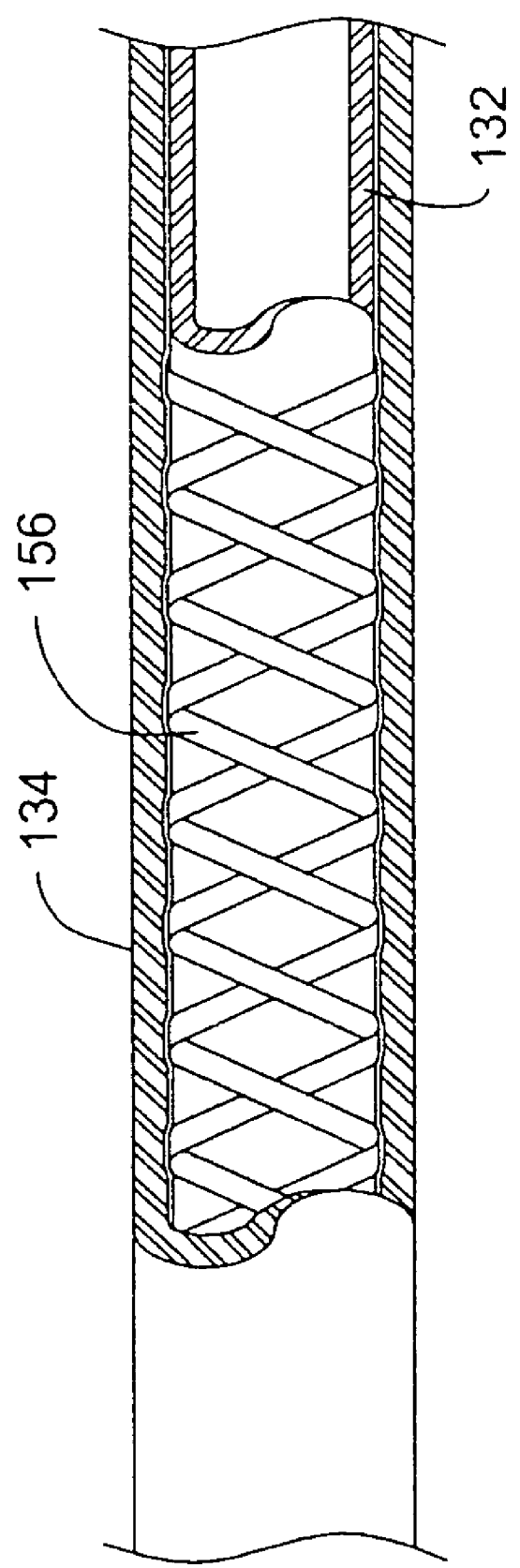
FIG. 6 is an enlarged side view of a catheter section having two ribbons interwoven to form a braid between an inner liner and an outer cover, with parts being broken away to show detail.

A catheter section having a stiffener comprising a braid member 156 interposed between the inner tubular liner 132 and the outer cover 134 is shown in FIG. 6. The braid member 156 may be made up of a suitable number of ribbons, typically four or more. The ribbons are interwoven in an in-and-out fashion as they cross to form a tubular member defining a single lumen. The pitch angle of the braid may be changed at the time the braid is woven or at the time the braid is included in the catheter section.

Figure 7:
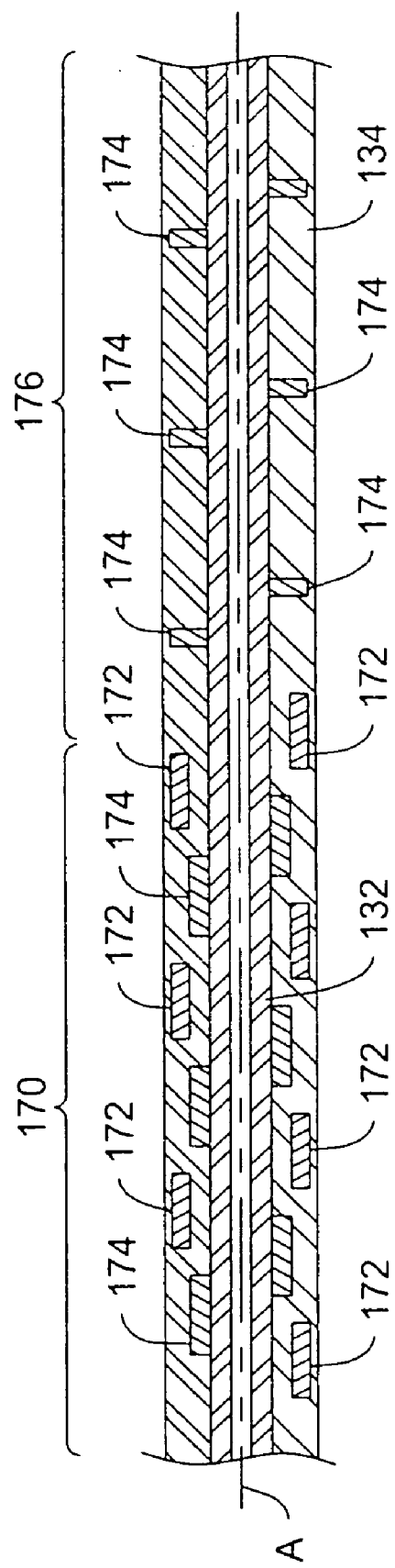
FIG. 7 is a schematic cross-sectional view of alternate proximal and distal sections of a catheter.

The coil and braid stiffeners shown in FIGS. 4–6 may be used alone or in combination to form a composite stiffener for the catheter of the present invention, as shown in FIGS. 2, 3, and 7, and described below.

The catheter portion of FIG. 2 includes first and second stiffeners which are both in the form of a helically wound coil. The second stiffener comprises a non-metal ribbon 142 helically wound in one direction on the inner liner 132 and the first stiffener comprises a metal ribbon 140 helically wound in an opposite direction on the second stiffener. An outer cover 134 is placed over the stiffeners. The metal ribbon 140 is only wound onto the proximal section of the catheter. This construction provides a reduction in stiffness in the distal section while providing a smooth transition between the two sections. In conventional catheters the proximal and distal sections often comprise two different stiffeners having different materials and different configurations. Since the only difference between the proximal section 124 and the distal section 128 is the elimination of the metal stiffener 140, there is no sharp transition which may affect catheter performance. The metal ribbon 140 in the proximal section provides kink-resistance, and increases the stiffness in the proximal section 124, thus improving pushability. The non-metal ribbon 142 in the distal section 128 provides kink-resistance and permits reshaping of the section upon exposure to steam, as previously discussed.

Figure 2A:
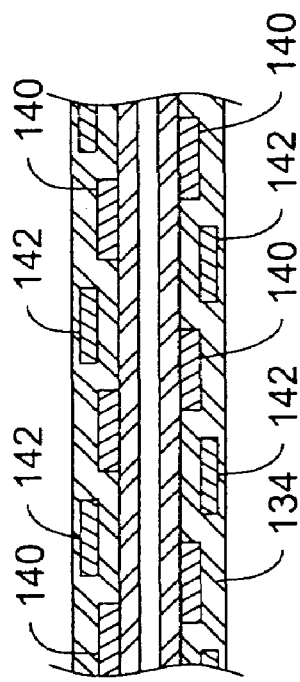
FIG. 2A is a cross-sectional view of an alternate portion of a catheter.

It is to be understood that the arrangement of the coils may be other than the one shown in FIG. 2. For example, as shown in FIG. 2A, the metal ribbon 140 may be first wound on the inner liner 132 and the non-metal ribbon 142 wound on top of the metal ribbon in the proximal section of the catheter. The non-metal ribbon 142 would then assist in holding down the metal ribbon 140. This lessens the tendency of the metal ribbon 140 to unwind and hence create bumps. The metal and non-metal ribbons 140, 142 may also be wound in the same direction, with ribbons being located adjacent one another. One or both of the stiffeners may also be formed with a double ribbon wind (not shown). For a double ribbon wind, a pair of ribbons is placed side by side and treated as a single ribbon. The braid is denser than the single ribbon wind. The number of ribbons, thickness of the ribbons, and pitch may also vary to further fine tune the stiffness of the catheter in the particular sections.

FIG. 3 schematically shows an alternative embodiment 122 of the catheter portion 120 of FIG. 2. The catheter portion 122 includes the inner liner 132, outer cover 134, a first stiffener, and a second stiffener interwoven to form a braid member. The first stiffener comprises a metal ribbon 160 and the second stiffener comprises a non-metal ribbon 162. The two ribbons 160, 162 are woven together in the proximal section 126 and when the distal section 130 is reached, the metal ribbon is terminated and only the non-metal ribbon is wound in the distal section. Instead of eliminating the metal ribbon 160 from the braid during the braiding process, the braid may be formed as a continuous member with both the metal and non-metal ribbons along the entire length of the braid member. The metal ribbon 160 may then be pulled from the braid in the distal section 130 during assembly of the catheter.

The braid may be interwoven from a single metal ribbon and a single non-metallic ribbon or a plurality of metal and non-metal ribbons. Commercial braiders are typically configured for producing eight or sixteen ribbon braids. The braid may be formed, for example, on a braider with four spools having metal ribbons and four spools having non-metal ribbons to produce a four stranded metal and four stranded non-metal braid. There may also be an uneven number of metal and non-metal ribbons (e.g., six metal ribbons and two non-metal ribbons). The metal and non-metal spools for the braider may be positioned such that the metal ribbons are all wound only in one direction with the non-metal ribbons wound in the opposite direction, or the spools may be positioned so that the metal and non-metal ribbons are intermixed with both type of ribbons being wound in each direction. It should be noted that if all non-metal ribbons are wound in only one direction, the distal section will have a coil stiffener rather than a braided stiffener. Alternatively, the first stiffener may comprise a braid formed from only metal ribbons and the second stiffener may comprise a braid formed from only non-metal ribbons. One braid is then positioned over the other braid in the proximal section, and only the non-metal braid is located in the distal section.

FIG. 7 schematically shows an alternative embodiment of the catheter portion 120 of FIG. 2. The catheter portion includes a proximal section 170 having a stiffener comprising a non-metal ribbon 174 helically wound on the inner liner 132. A metal ribbon 172 is helically wound on the non-metal ribbon 174. A distal section 176 of the catheter portion includes the non-metal ribbon 174 wound on the inner liner 132. The outer cover 134 is placed over the stiffeners in both the proximal and distal sections 170, 176. The non-metal ribbon 174 is wound in the proximal section 170 with the rectangular cross-section of the ribbon extending generally parallel to a longitudinal axis A of the catheter. The ribbon 174 is rotated in the distal section 176 so that the rectangular cross-section extends generally perpendicular to the longitudinal axis A. The ribbon 174 may also be wound in the proximal section 170 in the same orientation as in the distal section 176, for example. The non-metal ribbon 174 may also be positioned over the metal ribbon 172 in the proximal section, as previously discussed.

The metal stiffener is preferably formed from a metal alloy, such as stainless steel, tantalum or its alloys, tungsten, platinum, gold, copper, palladium, rhodium, or a superelastic alloy. Preferred superelastic alloys include the class of nickel/titanium materials known as nitinol, disclosed in U.S. Pat. Nos. 3,174,851, 3,351,463, and 3,753,700. Commercial alloys containing up to about 5% of one or more other members of the iron group, e.g., Fe, Cr, Co, are considered to be encompassed within the class of superelastic nickel/titanium alloys suitable for use. When using a superelastic alloy, an additional heat treat step may be desirable to preserve the shape of the stiffener. The stiffener is placed on a mandrel and then heated to a temperature of 650°–900° F. for a few minutes. After heat treatment, the stiffener retains its shape and the alloy retains its superelastic properties.

Desirable non-metal materials for the second stiffener include Pebax, Peek, polyimide, liquid crystal polymers (LCP) such as Vectran, polyethylene, polyethylene terephthalate and Nylon. Other suitable non-metallic materials include polymeric materials such as polyester, polypropylene, carbon fiber, polyaramids (e.g., KEVLAR), and lower performance polymers such as Dacron.

The ribbons are preferably between 0.3 mil. and 3.5 mil., and more preferably between 0.75 mil. and 1.5 mil. in thickness, and 2.5 mil. and 12.0 mil. in width. For superelastic alloys, particularly nitinol, the thickness and width may be somewhat finer, e.g., down to 0.5 mil. and 1.0 mil., respectively. The width of the ribbons may vary to provide specific stiffness requirements at different locations along the length of the catheter. The stiffeners may also be formed from a wire having a circular cross-sectional area.

Preferred polymeric materials for the inner liner 132 include fluoropolymers including PTFE, FEP, vinylidene fluoride, polyethylene, polyvinyl chloride (PVC), ethyl vinyl acetate (EVA), polyethylene terephthalate (PET), polyimide, polyamide, polypropylene, polyfluorocarbons, polyurethane (Carbothane), polyether block amide (Pebax), styrene-ethylene/butylene-styrene (SEBS), styrene-butadiene-styrene (SBS), polysulfone, and their mixtures, alloys, copolymers and block copolymers. Another useful class of polymers are theremoplastic elastomers, including those containing polyesters as components. Typical of this class is HYTREL. The inner liner 132 may be coated onto the inner surface of the stiffener. Polyesters and polyimides, in particular, are useful as adhesives in this service. The wall thickness of the inner liner 132 may be between 0.3 mil. and 3.0 mil., for example.

The outer cover 134 may be made of polyethylene or of EVA or their mixtures, for example. Preferred polymeric materials for the outer cover 134 include polyimide, polyamide, polyethylene, polyurethane, polyvinyl chloride, polypropylene, fluoropolymers including PTFE, FEP, vinylidene fluoride, and their mixtures, alloys, copolymers, and block copolymers. The polymer is typically extruded into a tubing of appropriate size and thickness and then crosslinked to raise the melt temperature of the resulting tubing. The tubing is then inflated and perhaps stretched to give the included polymer a specific molecular orientation. The tubing, so treated, may then be slipped over the combination of inner liner 132 and stiffener and heat shrunk into place. Heat shrunk tubing may be further heated to shrink the tubing in such a way that it fills the interstices between the windings of the ribbon. This allows the outer cover 134 to directly contact the inner tubular liner 132. Even more desirably, the outer cover 134 should be further heated to allow mixing of the outer cover with the inner liner 132 at their ineterface so as to form a strong integral catheter section. If a section with even more flexibility is required, the outer cover 134 may also be of a member selected from a more flexible material such as polyurethane (Carbothane), low density polyethylene (LDPE), polyvinyl chloride, polyurethane, polyether block amide (Pebax), styrene-ethylene/butylene-styrene (SEBS), styrene-butadiene-styrene (SBS), and other polymers of suitable softness or modulus of elasticity. The wall thickness of the outer cover 134 may be between 0.5 mil. and 10 mil., for example.

The outer cover 134 may also be applied by dipping the inner liner 132 and stiffener ribbon into a molten polymer bath or into a polymer dissolved in a solid or into a suspension or latex comprising the outer cover polymer. The outer cover 134 may also be placed on the catheter by spraying or otherwise applying the material.

The inner tubular liner 132 and outer cover 134 may each be formed as two separate members for the proximal and distal sections (i.e., proximal and distal inner tubular liners, and proximal and distal outer covers). The material of proximal inner tubular liner may be selected to have a higher stiffness than the material of the distal inner liner. The inner liner may also be omitted particularly in the more proximal section, since the majority of materials which are suitable for the more proximal section are very hard and suitably slippery for passage of guidewires 112 and the like.

It is to be understood that the materials and thickness of the inner liner 132 and outer cover 134 may be different than described herein without departing from the scope of the invention. Furthermore, each of the polymers noted herein may be used in conjunction with radiopaque filler materials such as barium sulfate, bismuth trioxide, bismuth carbonate, powdered tungsten, powdered tantalum, or the like so that the location of various portions of the catheter sections may be radiographically visualized within the human body.

The exterior surface of the outer cover 134 and the inner surface of the inner liner 132 may be coated with a lubricious layer which is chemically bonded or is physically coated on the surface. Polymers which inherently adhere to each other may be used for the inner liner 132 and outer cover 134 (e.g., certain polyethylenes and polyimides, or thermoplastics, which are miscible with one another upon appropriate heating, such as Pebax and polyurethanes). The exterior and interior surfaces of the catheter or catheter section may be coated with a lubricious layer such as a hydrophilic polymer layer, which is either chemically bonded to the layer or is physically coated on the surface.

The number and type of sections of the catheter may vary. The catheter sections may have multiple polymeric layers exterior of the stiffener as well as multiple polymeric liner members interior to the stiffener. The catheter sections may also include multiple layers of stiffeners between or amongst the various polymer layers.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A catheter comprising an elongate tabular member having a proximal end, a distal end, and a lumen extending therebetween, the lumen defined by an inner tubular liner, the elongate tubular member comprising:
    a relatively stiff proximal section comprising a metallic stiffener and a non-metallic stiffener, the metallic and non-metallic stiffeners being coaxially wound exterior to a proximal portion of the inner tubular liner; and
    a relatively flexible distal section comprising the non-metallic stiffener coaxially wound exterior to a distal portion of the inner liner, the metallic stiffener terminating before reaching the distal section such that the distal section is devoid of a metallic stiffener.

2. The catheter of claim 1, wherein the non-metallic stiffener is interposed between the inner tubular liner and the metallic stiffener.

3. The catheter of claim 1, wherein the metallic stiffener is interposed between the inner tubular liner and the non-metallic stiffener.

4. The catheter of claim 1, Wherein the metallic stiffener is a helically wound ribbon.

5. The catheter of claim 1, wherein the non-metallic stiffener is a helically wound ribbon.

6. The catheter of claim 1, wherein the metallic stiffener is helically wound in one direction and the non-metallic stiffener is helically wound in an opposite direction.

7. The catheter of claim 1, wherein the metallic and non-metallic stiffeners are interwoven to form a braid member.

8. The catheter of claim 7, wherein the metallic and non-metallic sniffeners each comprise a ribbon.

9. The catheter of claim 8, wherein the ribbons have a thickness of between about 0.3 mil. and about 3.5 mil. and a width between about 2.5 mil. and about 12.0 mil.

10. The catheter of claim 1, wherein the non-metallic stiffener comprises a material capable of undergoing permanent deformation upon exposure to steam.

11. The catheter of claim 1, wherein the non-metallic stiffener comprises a polymer.

12. The catheter of claim 11, wherein the polymer comprises a liquid crystal polymer.

13. The catheter of claim 11, wherein the polymer comprises a material selected from the group consisting of polyimide, polyethylene, polyethylene terephthalate, and Nylon.

14. The catheter of claim 1, wherein the metallic stiffener comprises a superelasric alloy.

15. The catheter of claim 11, wherein the superelasric alloy comprises nickel and titanium.

16. The catheter of claim 1, wherein the metallic stiffener comprises stainless steel.

17. The catheter of claim 1, wherein the metallic stiffener comprises a material selected from the group consisting of gold, platinum, and copper.

18. The catheter of claim 1, wherein the metallic stiffener comprises a platinum-tungsten alloy.

19. The catheter of claim 1, wherein the inner tubular liner comprises a proximal portion and a distal portion, and the proximal and distal portions each comprise a polymer.

20. The catheter of claim 19, wherein the polymer is selected from the group consisting of polyimide, polyamide, polyester, polyethylene, polypropylene polyvinyl chloride, polytluorocarbons, polyurethane, polysulfone, ethyl vinyl acetate, polyether block amide, styrene-ethylenelbutylene-styrene, styrene-butadiene-styrene, polyethylene terephihalate, and their mixtures, alloys, blends, copolymers, and block copolymers.

21. The catheter of claim 1, wherein the proximal section comprises a proximal outer cover exterior to the metallic and non-metallic stiffeners, and the distal section comprises a distal outer cover exterior to the non-metallic stiffener.

22. The catheter of claim 21, wherein the proximal and distal outer covers comprise a material selected from the group consisting of polyamide, polyamide, polyether block amide, styrene-ethylen/butylene-styrene, styrene-butadiene-styrene, polyethylene, polypropylene, polyvinyl chloride, fluoropolymers, vinylidene fluoride, polyurethane, and their mixtures, alloys, copolymers, and block copolymers.

23. The catheter of claim 21, wherein the proximal and distal outer covers are integrally formed and comprise a polymer which can be heat-shrunk onto the metallic and non-metallic stiffeners.

24. The catheter of claim 21, wherein at least one of the inner tubular liner and the outer coven are radiopaque.

25. The catheter of claim 1, further comprising a removable, slidable guidewire placed interior to and in slidable relationship to the distal and proximal sections.

26. The catheter of claim 1, wherein the non-metallic stiffener comprises a helically wound ribbon having a rectangular cross-section extending generally parallel to a longitudinal axis of the catheter in the proximal section, and extending generally perpendicular to the longitudinal axis of the catheter in the distal section.

27. A catheter comprising an elongate tubular member having a proximal end, a distal end, and an inner lumen therebetween, the inner lumen defined by an inner tubular liner, the elongate tubular member comprising:
 a relatively stiff proximal section comprising a proximal braid member comprising at least one metal strand interwoven with at least one non-metal strand, and a proximal outer cover, the at least one metal strand and the at least one non-metal strand of the braid being coaxially wound exterior to the inner tubular liner; and
 a relatively flexible distal section comprising the inner tubular liner and a distal braid member comprising the at least one non-metal strand of the proximal braid member, and a distal outer cover, the at least one metal strand of the proximal braid member terminating before reaching the distal section, such that the distal section is devoid of the at least one metal strand of the proximal braid member.

28. The catheter of claim 27, wherein the metal strand and the non-metal strand each comprise a ribbon.

29. The catheter of claim 28, wherein the ribbons have a thickness of between about 0.5 mil. and about 3.5 mil. and a width between about 2.5 mil. and about 12.0 mil.

30. The catheter of claim 27, wherein the at least one metal strand comprises four metal strands and the at least one non-metal strand comprises four non-metal strands.

31. The catheter of claim 27, wherein the non-metal strand comprises a polymer.

32. The catheter of claim 31, wherein the polymer comprises a liquid crystal polymer.

33. The catheter of claim 31, wherein the polymer comprises a material selected from the group consisting of polyimide, polyethylene, polyethylene terephthalate, and Nylon.

34. The catheter of claim 27, wherein the metal strand comprises a superelastic alloy.

35. The catheter of claim 34, wherein the superelastic alloy comprises nickel and titanium.

36. The catheter of claim 27, wherein the metal strand comprises stainless steel.

37. The catheter of claim 27, wherein the metal strand comprises a platinum-tungsten alloy.

38. The catheter of claim 27, wherein the inner tubular liner and the proximal and distal outer covers comprise a polymer.

39. The caterer of claim 27, further comprising a removable, slidable guidewire placed interior to and in slidable relationship to the distal and proximal sections.

40. The catheter of claim 27, wherein the distal section is disposed at the distal end of the catheter.

41. A catheter comprising an elongate tubular member having a proximal end, a distal end, and a lumen extending therethrough, the catheter comprising:
 a proximal section comprising a metallic stiffener interwoven with a non-metallic stiffener to form a braid member; and
 a distal section comprising the non-metallic stiffener of the proximal section, and wherein the metallic stiffener of the proximal section terminates proximal the distal section such that the distal section is devoid of a metallic stiffener.

* * * * *

UNITED STATES PATENT AND TRADEMARK OFFICE
CERTIFICATE OF CORRECTION

PATENT NO. : 7,104,979 B2
APPLICATION NO. : 10/079103
DATED : September 12, 2006
INVENTOR(S) : Lex P. Jansen et al.

It is certified that error appears in the above-identified patent and that said Letters Patent is hereby corrected as shown below:

Column 7
Line 21, delete "theremoplastic" and insert therefor -- thermoplastic --

Column 8
Line 42, delete "tabular" and insert therefor -- tubular --.

Column 9
Line 5, delete "sniffeners" and insert therefor -- stiffeners --.
Line 21, delete "superelasric" and insert therefor -- superelastic --.
Line 22, delete "superelasric" and insert therefor -- superelastic --.
Line 37, delete "polytluorocarbons" and insert therefor -- polyfluorocarbons --.
Line 38, delete "styrene-ethylenelbutylene-styrene" and insert therefor -- styrene-ethylene/butylene-styrene --.
Lines 39-40, delete "terephihalate" and insert therefor -- terephthalate --.
Line 48, delete "polyamide, polyamide" and insert therefor --polyimide, polyamide --.
Line 58, delete "coven" and insert therefor -- covers --.

Column 10
Line 48, delete "caterer" and insert therefor -- catheter --.

Signed and Sealed this

Ninth Day of January, 2007

JON W. DUDAS
*Director of the United States Patent and Trademark Office*